United States Patent [19]

Katakura

[11] Patent Number: 5,535,747
[45] Date of Patent: Jul. 16, 1996

[54] ULTRASONIC EQUIPMENT

[75] Inventor: Kageyoshi Katakura, Tokyo, Japan

[73] Assignee: Hitachi, Ltd., Tokyo, Japan

[21] Appl. No.: 397,990

[22] Filed: Mar. 3, 1995

[30] Foreign Application Priority Data

Mar. 4, 1994 [JP] Japan ................................ 6-034408

[51] Int. Cl.$^6$ ................................ A61B 8/00; A61B 8/06
[52] U.S. Cl. ................................ 128/660.02; 128/661.08
[58] Field of Search ............ 128/660.02, 661.07–661.1, 128/680–682; 73/861.25, 861.27, 861.31

[56] References Cited

U.S. PATENT DOCUMENTS

| 3,640,271 | 2/1972 | Horton | 128/660.02 |
| 4,483,345 | 11/1984 | Miwa | 128/660.02 |
| 5,411,028 | 5/1995 | Bonnefous | 128/660.02 X |
| 5,450,850 | 9/1995 | Iinuma | 128/661.09 |

Primary Examiner—Francis Jaworski
Attorney, Agent, or Firm—Antonelli, Terry, Stout & Kraus

[57] ABSTRACT

The ultrasonic apparatus has a transmitter for transmitting an ultrasonic wave filled with a fluid from the outside of a pipe, a receiver for receiving echo signals from the inside of the pipe, a pulse wave propagation time measuring instrument for estimating a propagation time of a pulse wave between a plurality of measurement points within the tube on the basis of the echo signals from the measurement points, a pulse wave velocity estimator for estimating a speed of the pulse wave from the propagation time of the pulse wave and the distance between the measurement points, a flow speed estimator for measuring a flow speed of the fluid within the pipe, and a pressure estimator for measuring a pressure of the fluid within the pipe at a particular time, whereby the absolute value of a pressure at another time different from the particular time is estimated from the flow speed of the fluid within the pipe which is produced from the flow speed estimator and the pressure of the fluid at the particular time which is produced from the pressure estimator.

8 Claims, 3 Drawing Sheets

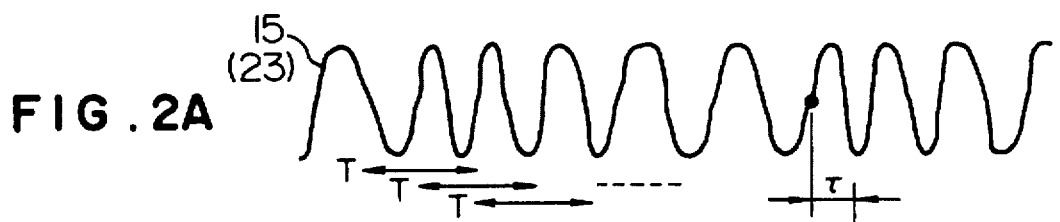
FIG. 2A
FIG. 2B
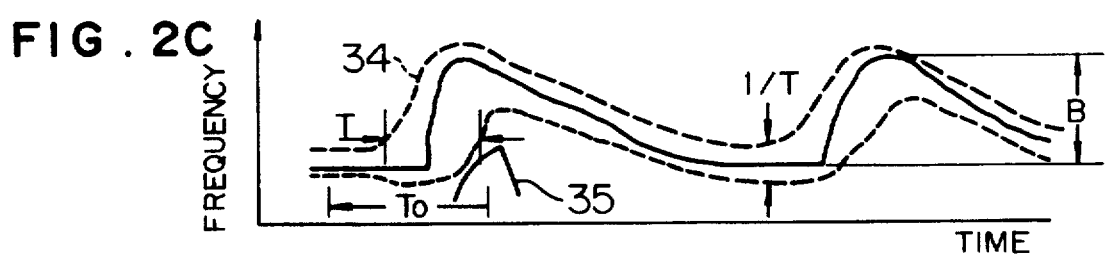
FIG. 2C
FIG. 2D
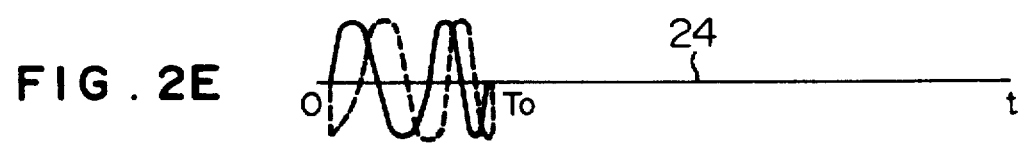
FIG. 2E
FIG. 2F

ULTRASONIC EQUIPMENT

BACKGROUND OF THE INVENTION

This invention relates to ultrasonic equipment for measuring the propagation velocity of an ultrasonic pulse wave propagating within a blood vessel so as to make continuous measurement of absolute blood pressure.

There is known a technique for measuring the propagation velocity of the pulse, wave (called pulse wave speed) on the basis of the deformation of blood wall or of the time lag between blood flow Doppler signal waveforms at two far-separated points. For example, an ultrasonic pulse wave speed estimator is described in JP-A-62-26050. According to this speed estimator, information related to changes of reflected ultrasonic waves with respect to time is obtained at two points on the blood wall along the pipe, a time difference between the changes at the two points is measured from this information and the pulse wave speed is calculated on the basis of the time difference and the distance between the two points.

Also, a B-mode interlocking-type ultrasonic small displacement measuring instrument is described in Inst. Elec. Inf. Com. Eng. Tec. Rep., MBE 84–17, pp. 9–16 (1984). According to this document, the phase of echo signal is followed by use of a zero-crossing point tracking function and a very small displacement of tissue is measured to thereby obtain physical information such as hardness as well as morphologic information. As is described in the above document, this instrument is also used to make non-invasive measurement for local blood vessel elasticity, or blood vessel elasticity distribution using the pulse.

In addition, measurement of mean pulse wave speed in artery throughout body by use of ultrasonic Doppler blood flow wave is described in Proc. of Jpn. Soc. Ultrason. Med. 51-PB-31, pp. 231–232 (Nov. Showa 62 (1987)). According to this document, the pulse waves in carotid artery and femoral artery are simultaneously recorded, the mean pulse wave speed calculated by use of the time difference therebetween is compared with that of blood flow wave recorded at the same position.

SUMMARY OF THE INVENTION

In the conventional ultrasound tomography using the normal echo signals, it is impossible to draw smaller blood vessels than spatial resolution. However, if Doppler means is used, blood movement information makes it possible to discriminate blood vessels from the surroundings so that the blood flow in fine blood vessels can also be detected. The measurement of blood flow by Doppler effect is normally carried out by Fourier analysis of changes of echo signal frequency due to Doppler effect. In this case, however, the resolution of time is limited by integration time of Fourier transformation because of uncertainty relation of time and frequency resolution in Fourier transformation. In normal case, time resolution of about 100 msec or below cannot be achieved.

It is an object of the invention to provide an ultrasonic apparatus capable of solving the above problems, or remarkably improving the precision with which the propagation time of pulse wave is measured, measuring the propagation time of pulse wave between two close points, and continuously measuring the absolute value of blood pressure in deep seated vessels.

The ultrasonic apparatus of the invention, in order to be applied to the measurement even for small blood vessels, fundamentally employs Doppler signals for the measurement, considers the wide-band characteristic of the blood flow Doppler signals, and measures the delay time by the correlation processing of the Doppler signals. According to this construction, the precision of the measurement of pulse wave propagation time can be remarkably improved, and the absolute value of the blood pressure can be measured by using the relation among the pulse wave speed, blood flow speed and blood pressure change.

In other words, the first feature of the ultrasonic apparatus of the invention resides in the fact that it has a transmitter for transmitting an ultrasonic wave into the inside of a blood vessel being inspected, a receiver for receiving echo signals from the inside of the blood vessel, pulse wave propagation time measuring means for estimating the propagation time of a pulse wave between a plurality of measurement points in the inside of the blood vessel on the basis of the echo signals from the measurement points, a pulse wave speed estimator for estimating the pulse wave speed from the propagation time of the pulse wave and the distance between the measurement points, flow speed measuring means for measuring the flow speed of the blood flow, a blood pressure estimator for measuring a blood pressure at a particular time of cardiac phase, and an absolute blood pressure estimator for estimating the absolute value of a blood pressure at another time different from the particular time on the basis of the flow speed of the blood flow which is produced from the flow speed measuring means and the blood pressure which is produced from the blood pressure estimator at the particular time.

The second feature of the ultrasonic apparatus of the invention resides in the fact that it has a transmitter for transmitting an ultrasonic wave into the inside of a blood vessel being inspected, a receiver for receiving echo signals from the inside of the blood vessel, and pulse wave propagation time measuring means for estimating the propagation time of a pulse wave between a plurality of measurement points within the blood vessel on the basis of variations of Doppler signals of the echo signals from the measurement points with respect to time, whereby the speed of the pulse wave is calculated from the propagation time of the pulse wave and the distance between the measurement points, this ultrasonic apparatus further including a correlator for calculating a correlation function between the Doppler signals, flow speed measuring means for estimating the propagation time of the pulse wave by use of the correlation function and measuring the flow speed of the blood flow, a blood pressure estimator for measuring a blood pressure at a particular time, and an absolute blood pressure estimator for estimating the absolute value of a blood pressure at another time different from the particular time on the basis of the blood flow speed from the flow speed measuring means and the blood pressure at the particular time which is produced from the blood pressure estimator.

In the ultrasonic apparatus having the first and second features, the blood pressure at the particular time is an end diastolic blood pressure.

The third feature of the ultrasonic apparatus of the invention resides in the fact that it has a transmitter for transmitting an ultrasonic wave into the inside of a pipe filled with a fluid from the outside of the pipe, a receiver for receiving echo signals from the inside of the pipe, pulse wave propagation time measuring means for estimating the propagation time of a pulse wave between a plurality of measurement points within the pipe on the basis of the echo signals from the measurement points, pulse wave speed measuring means for estimating the pulse wave speed from the propagation time of the pulse wave and the distance between the measurement points, flow speed measuring means for measuring the flow speed of the fluid within the pipe, a pressure estimator for measuring a pressure of the fluid within the pipe at a particular time, and an absolute pressure estimator for estimating the absolute value of a pressure of the fluid within the pipe at another time different from the particular time on the basis of the flow speed of the fluid within the pipe which is produced from the flow speed measuring means and the pressure of the fluid at the particular time which is produced from the pressure estimator.

The fourth feature of the ultrasonic apparatus of the invention resides in the fact that it has a transmitter for transmitting an ultrasonic wave into the inside of a pipe filled with a fluid from the outside of the pipe, a receiver for receiving echo signals from the inside of the pipe, and pulse wave propagation time measuring means for calculating the propagation time of a pulse wave between a plurality of measurement points within the pipe on the basis of variations of Doppler signals of the echo signals from the measurement points with respect to time, whereby the pulse wave speed is calculated from the propagation time of the pulse wave and the distance between the measurement points, this ultrasonic apparatus further including a correlator for calculating a correlation between the Doppler signals, flow speed measuring means for estimating the propagation time of the pulse wave by use of the correlation function and measuring the flow speed of the fluid within the pipe, a pressure estimator for measuring a pressure of the fluid within the pipe at a particular time, and an absolute pressure estimator for estimating a pressure of the fluid at another time different from the particular time on the basis of the flow speed of the fluid within the pipe which is produced from the flow speed measuring means and the pressure of the fluid at the particular time which is produced from the pressure estimator.

In the ultrasonic apparatus having the third and fourth features, the fluid within the pipe is a liquid which is pressed to be fed into the inside of the pipe by a pump.

In the conventional ultrasound tomography using normal echo signals, it is impossible to draw small blood vessels which size is below the spatial resolution. However, if Doppler method is used, blood movement information makes it possible to discriminate blood vessels from the surroundings so that the blood flow in fine blood vessels can also be detected. The measurement of blood flow by Doppler effect is normally carried out by Fourier analysis of changes of echo signal frequency due to Doppler effect. In this case, however, the resolution of time is limited by integration time of Fourier transformation because of uncertainty relation of time and frequency resolution in Fourier transformation. In normal case, time resolution of about 100 msec or below cannot be achieved.

By the way, it is known that the time resolution of the correlation function is about (1/B) sec (B is the frequency bandwidth:Hz). In addition, the bandwidth of the Doppler signals in the normal blood vessel is 1 kHz or above. Thus, in this invention, the reciprocal of this frequency bandwidth, or the time resolution of 1/1000 sec (1 msec) is achieved by the correlation processing between the blood flow Doppler signals for the measurement of time difference. On the other hand, since the pulse wave speed in a living body is changed from 4 m/sec to about 10 m/sec, the time required for the pulse wave to pass a distance of 10 cm is in a range from 25 msec to 10 msec. Therefore, since the time resolution in this invention is 1 msec, the propagation time of the pulse wave even in the distance of as narrow as 10 cm can be measured with a satisfactory precision, and hence the local pulse wave speed can be measured. This pulse wave speed C, a flow speed variation of blood, $\Delta V$ and the amount of change of blood pressure, $\Delta P$ have the following relation $$\Delta P = \rho C \Delta V \quad (1)$$

where $\rho$ is the density of blood. In this invention, a normal cuff type hemonanometer or the like is used to measure the absolute value of a blood pressure $P_0$ at a particular time such as an end diastolic blood pressure or a blood pressure generally called minimum blood pressure.

The term, particular time, given here is used when the pressure of a generally pulsatively pressure-changing fluid exhibits a particular pressure at that particular time, and in this case the fluid may be flowing or not. The absolute value P of a blood pressure at an arbitrary time can be calculated by substituting the above-mentioned absolute pressure $P_0$ into the following equation:

$$P = P_0 + \Delta P = P_0 + \rho C \Delta V \quad (2)$$

The change of blood flow speed, $\Delta V$ is determined by the amount of frequency shift on the Doppler blood flow meter.

By measuring the local propagation speed of the pulse wave of ultrasonic wave propagating in a blood vessel and using the measured value of the blood pressure at a particular time together with the propagation speed of the pulse wave, it is possible to make temporal measurement, on a non-invasive basis, of the absolute value of a changing blood pressure even for local small vessels and deep seated artery. The term, particular time mentioned above is also used when the pressure of a generally pulsatively pressure-changing fluid exhibits a particular pressure at that particular time.

BRIEF DESCRIPTION OF THE DRAWINGS

FIGS. 2A, 2B, 2C, 2D, 2E and 2F show waveforms of signals at respective portions which constitute the ultrasonic apparatus of the invention.

DESCRIPTION OF THE PREFERRED EMBODIMENTS

The present invention will be described in detail with reference to the accompanying drawings.

Figure 1:
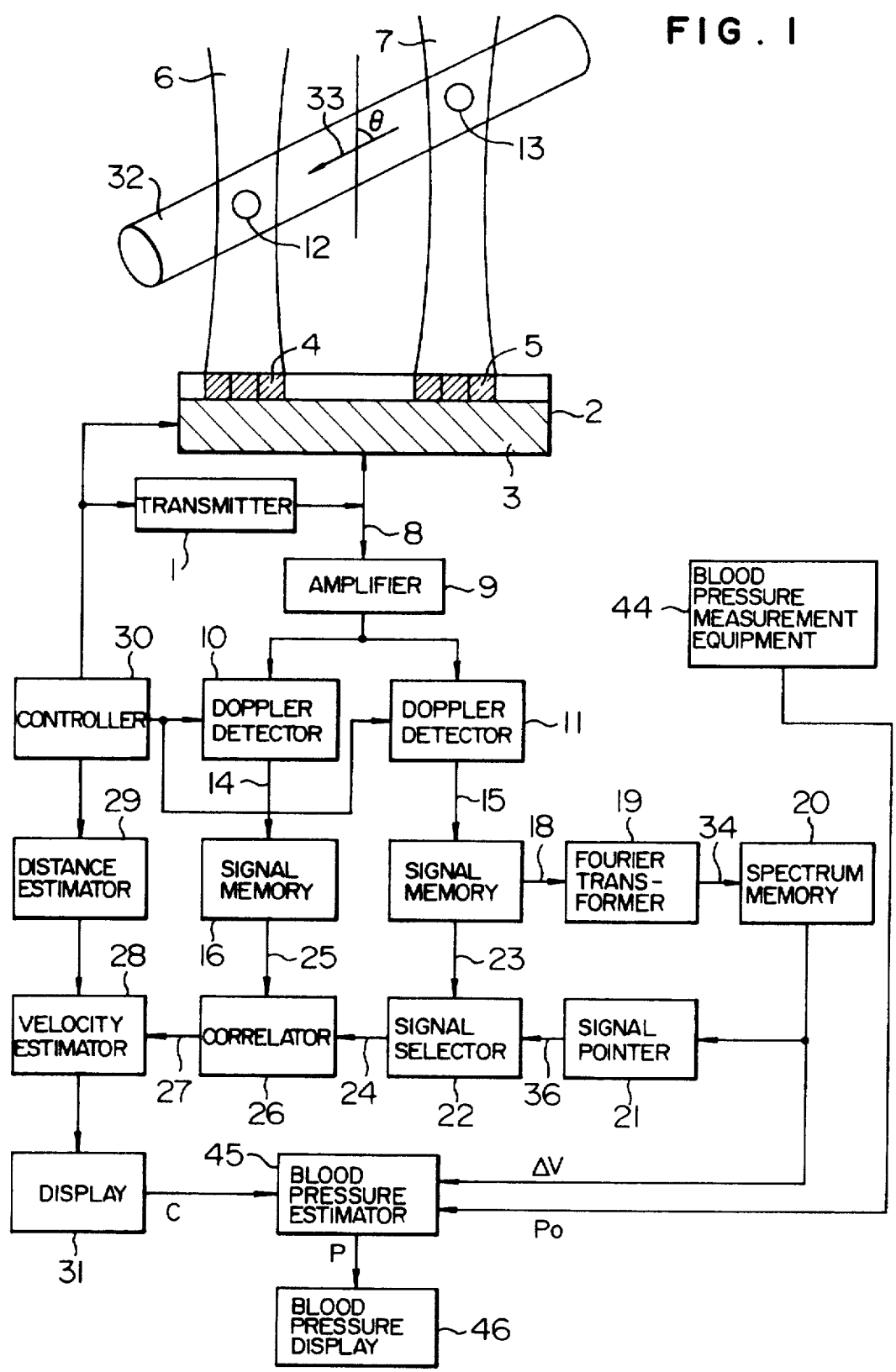
FIG. 1 is a block diagram of the construction of the ultrasonic apparatus according to this invention.

The basic operation of this invention will be mentioned in detail with reference to FIG. 1 in which one embodiment of the invention is shown. Referring to FIG. 1, a pulse-shaped electrical signal is generated from a transmitter 1 and supplied to an array transducer 2. A selection switch 3 provided within this array transducer selects a group 4 or 5 of transducer elements alternately. An ultrasound beam 6 or 7 is alternately generated and an echo signal from the corresponding region is produced as a received signal 8. This received signal 8 is amplified by an amplifier 9 and fed to Doppler detectors 10 and 11 for extracting Doppler signals 14, 15. The portions up to the Doppler detectors are used to extract Doppler signals from each of the echo signals of ultrasound beams 6, 7 which are reflected from measurement points 12, 13, according to the so-called pulse Doppler method. The Doppler signals 14, 15 thus produced, corresponding to the signals from the measurement points are once stored in signal memories 16, 17. A partial waveform 18 of a temporary signal 23 which has been once stored in the signal memory 17 is transformed into Fourier series by a Fourier transformer 19 in turn and stored in a spectrum memory 20 as a Doppler time sequence frequency spectrum. A signal pointer 21 is used to select a wide-band signal portion from the contents of the spectrum memory 20. On the basis of this result of judgement, a signal selector 22 selects only a particular portion of the temporary signal 23 which has been stored in the signal memory 17. This particular signal portion is used as a reference signal 24. The correlator 26 calculates a correlation function 27 between this reference signal 24 and a temporary signal 25 of the contents of the other signal memory. The movement time τ (FIG. 2F) of the maximum value appearance time from the origin corresponds to the propagation time of the pulse wave between the measurement points 12 and 13. A velocity estimator 28 measures this propagation time and divides by it the distance between the measurement points 12 and 13 which is determined by a distance estimator 29, thereby calculating the velocity. A controller 30 is used to set the spatial positions of ultrasound beams and the distance from the array transducer to the measurement points 12, 13. The information of the fixed values is fed to the distance estimator 29 so that the distance estimator 29 can calculate the distance between the measurement points. The pulse wave speed thus decided is displayed on a display 31. In FIG. 1, 32 is the flow pass of blood vessel (blood flow position) of interest, and 33 is the flow direction. In addition, θ indicates the angle of the flow direction to the ultrasound beams.

The operation of each portion will be described in more detail with reference to the signal waveform in each case. The output signals from the Doppler detectors 10, 11 are the Doppler signals 14, 15 corresponding to the measurement points 12, 13, respectively. These signals are shown in FIGS. 2A and 2B. The instantaneous frequencies of both signals change in like manner in accordance with the flow speed. The frequency variation of the Doppler signal 15 down the flow is delayed, relative to the Doppler signal 14 up the flow, by the pulse wave propagation time τ which corresponds to the distance between the measurement points 13 and 12. The propagation time of pulse wave, τ is expressed by the following equation.

$$\tau = L/C \tag{3}$$

where L is the distance between the measurement points and C is the pulse wave speed.

These Doppler signals 14, 15 are stored in the signal memories 16, 17, respectively. When these waveforms are transformed into Fourier series, the result for the signal 15 of FIG. 2A is shown in FIG. 2C, and the result for the signal 14 of FIG. 2B is shown in FIG. 2D. Here, as shown in FIGS. 2A and 2B, the integration time of Fourier transformation is represented by T and the waveform within time T is transformed into Fourier series. The actual frequency changes of the Doppler signals are indicated by the solid lines in FIGS. 2C and 2D. However, when frequency analysis is made over the integration time T, the frequency resolution is generally 1/T and the time resolution is T. Thus, the output signals are distributed within the range between the two dotted lines in FIGS. 2C and 2D. Therefore, it is difficult to determine the mutual time difference τ with high precision from these results of Fourier transformation. Thus, according to this invention, the partial waveform 18 in the signal memory 17 is transformed into Fourier series by the Fourier transformer 19 so that frequency spectrum information 34 can be obtained as shown in FIG. 2C. This frequency spectrum information 34 is stored in the spectrum memory 20. The signal pointer 21 detects a location of wide frequency change, 35 from the spectrum information of the spectrum memory 20. This detecting means may be of any construction such as automatic type or visual type. The width of frequency change can be given by the following equation.

$$B = 2f \times \Delta V \times \cos\theta / c (Hz) \tag{4}$$

where ΔV (m/sec) is the amount of change of flow speed, f(Hz) is the frequency of the ultrasonic wave used, and c is the propagation speed of the ultrasonic wave, or about 1500 m/sec in water.

If the amount of change of flow speed is 1.5 m/sec, the ultrasonic wave frequency used is 1 MHz, and θ is 0 degree, then the frequency variation width B is 2000 Hz. A temporal gate signal 36 for selecting the location of wide frequency change ($T_0$ shown in FIG. 2C) 35 is supplied to the signal selector 22. The signal selector 22 is controlled by this temporal gate signal 36 to extract only the time component corresponding to the location of wide frequency change 35 from the temporary signal 23 and to produce it as the reference signal 24.

The reference signal 24 is shown in FIG. 2E. Although the signals have so far been treated as real signals for convenience of explanation, the Doppler signals 14, 15 are actually complex signals since the normal Doppler measurement is made on complex signals. Thus, the reference signal 24 is also a complex signal having orthogonal components as indicated by broken lines and solid lines in FIG. 2E. Therefore, the actual processing for the Doppler measurement and for the following is made on all complex signals. The correlation function between the complex reference signal 24 and the temporary signal 25 having the same shape as the Doppler signal 14 is calculated by the correlator 26. The output from the correlator is a correlation function R(σ) 27 shown in FIG. 2F. The time lag τ between the Doppler signals 14 and 15 is determined by the maximum position in the correlation function R(σ) 27. Here, the maximum width is 1/B (sec) where B is 2000 Hz, and hence 1/2000=0.5 msec which means high precision for time measurement. The velocity estimator 28 calculates the pulse wave speed C from the time τ and the distance L between measurement points according to the following equation.

$$C = L/\tau \tag{5}$$

The result is indicated on the display 31.

The operation of the correlator 26 will be described below. The signal shown in FIG. 2E is represented by a(t) and expressed by the following equation.

$$a(t) = u(t) \exp\{j\theta_a(t)\} \tag{6}$$

In addition, the temporary signal 25 is represented by b(t) and expressed by the following equation.

$$b(t) = v(t) \exp\{j\theta_b(t)\} \tag{7}$$

Figure 3:
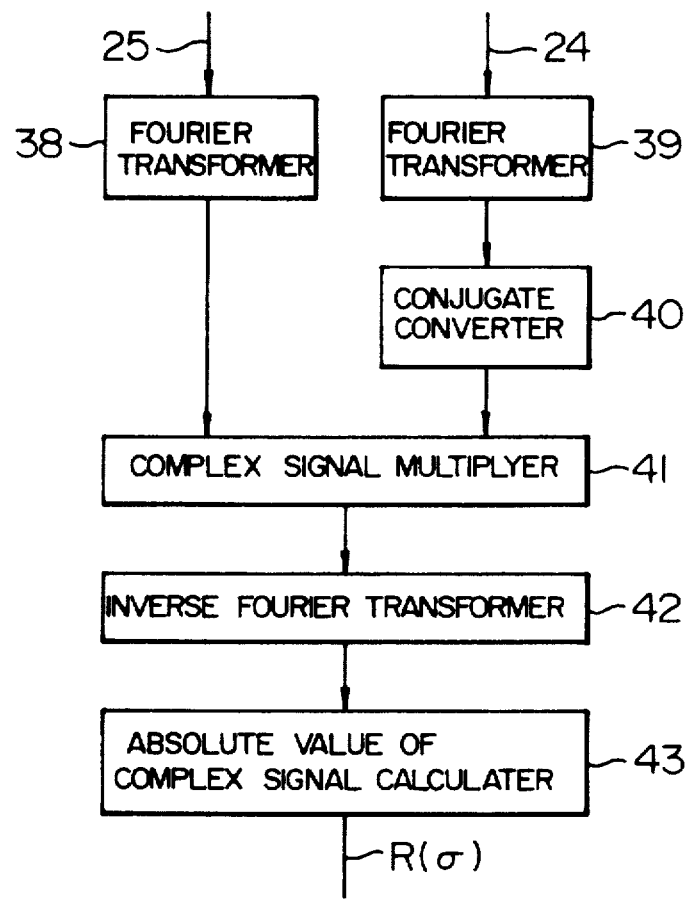
FIG. 3 is a block diagram of an example of the construction of a correlator of the ultrasonic apparatus of the invention.

At this time, the output R(σ) from the correlator 26 can be expressed by $$R(\sigma) = |\int <a(t)> b(t+\sigma) \, dt| \tag{8}$$

where $<a(t)>$ is the conjugate of $a(t)$, and the integration is made over the range from 0 to $T_0$. In addition, the relation of well-known Fourier transformation is used as shown in FIG. 3. That is, both signals are transformed into Fourier series by the Fourier transformers 38, 39, one of both outputs is fed to a conjugate converter 40 by which it is converted into a conjugate complex, and a complex signal multiplier 41 makes the product of the output from the Fourier transformer 38 and the output from the conjugate converter 40. Then, the product is converted back by an inverse Fourier transformer 42 to produce a correlation function, and finally the correlation function is fed to an absolute-value-of-complex-signal calculator 43 by which the absolute value of complex signal can be produced as output $R(\sigma)$. In the construction in which Fourier transformation is once made as mentioned above, it is also possible to selectively suppress the unnecessary frequency components such as DC component before the inverse Fourier transformation. Moreover, the correlator may be sometimes simply constructed by selecting one of the input signals as a real number. In this case, for example, the equation of $$a(t)=u(t)\exp\{j\theta_a(t)\} \quad (9)$$

is satisfied, the temporal signal 25 is selected to be only the real number of $b(t)$, and the following equation is satisfied.

$$c(t)=\text{Real }\{b(t)\}=v(t)\cos\{\theta_b(t)\} \quad (10)$$

At this time, the output $R(\sigma)$ from the correlator 26 is simply calculated from $$R(\sigma)=|\int c(t)b(t+\sigma)dt| \quad (11)$$

where the integration is made over the range from 0 to $T_0$.

Figure 4:
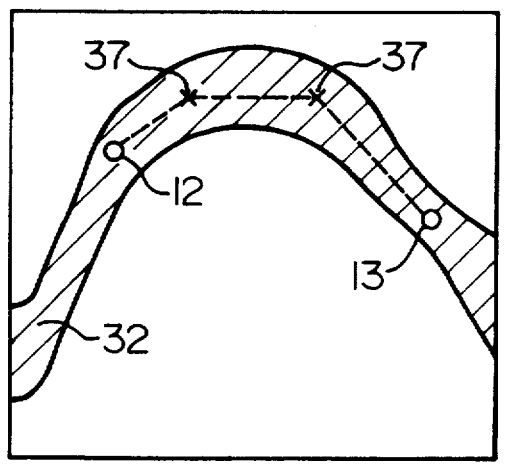
FIG. 4 is a graph showing one example of the measurement of distance between measurement points by the ultrasonic apparatus of the invention.

The time resolution in the correlation is enhanced in proportion to the frequency bandwidth of signal. Therefore, the frequency characteristic is corrected for a frequency band in which the signal exists; for example, if the high-frequency region and low-frequency region are emphasized, the resolution can be improved. While this embodiment actually uses complex signals, it is not limited to use of complex signals, but may be of any construction in which only the real part or imaginary part can be used. In addition, the distance between measurement points along a curved path can also be correctly measured together with cursor, marker or pointer 37 as shown by the picture of the distance estimator 29 in FIG. 4. This distance estimator is of course combined with the display for images by ultrasound tomography or three-dimensional images, but its construction can be applied to all the known electronic selector, electronic linear, convex scanners and so on. The combination with color Doppler equipment is also very useful in detection of minute blood vessels.

On the other hand, a blood pressure $P_0$ at a particular time from a blood pressure measurement equipment 44 and the amount of change of blood flow, $\Delta V$ calculated from $$\Delta V=B\times c/(2f\times\cos\theta)(\text{m/sec}) \quad (12)$$

which equation is derived from Eq. (4), on the basis of the spectrum information from the spectrum memory 20 are simultaneously supplied to a blood pressure estimator 45, which then calculates the absolute pressure P from the equation (2). The calculation result is indicated on a blood pressure display 46. As expressed by the equation (12), the change of blood speed, $\Delta V$ is determined from the frequency variation width B on the Doppler blood flow meter. The blood pressure display 46 indicates the continuously measured and changing absolute pressure P with respect to the time base. For example, it can be displayed in the form shown by the solid line in FIG. 2(C).

While measurement of blood within a blood vessel, for instance, has been described above, the system of this invention is not limited to the blood within a vessel, but may be applied to the measurement of pressure of various fluids such as cooling water which is forced to flow within a pipe (tube) by a pump. As described above, a particular pressure (a fluid pressure at a particular time) and flow speed of a pulse-like pressure-changing fluid are used to determine a fluid pressure at another time different from the particular time. In the system of this invention, the fluid within a pipe may either flow or stand still.

The construction of the ultrasonic apparatus of the invention which is capable of measuring absolute blood pressure can be summarized as follows. The Doppler signals 14, 15 are stored in the signal memories 16, 17. The partial waveform 18 of the temporary signal 23 is transformed into Fourier series and stored in the spectrum memory 20. The signal pointer 21 selects a wide-band signal portion from the stored contents. A particular portion of the temporary signal 23 is selected as the reference signal 24 by the signal selector 22. The correlator 26 calculates the correlation function 27 from the reference signal 24 and, the temporary signal 25. The velocity estimator 28 measures the pulse wave propagation time between the measurement points 12 and 13 and calculates the speed from it and the distance between the measurement points 12 and 13 which is fed from the distance estimator 29. The blood pressure estimator 45 estimates the absolute value of blood pressure from the speed from the velocity estimator 28, the blood pressure from the blood pressure measurement equipment 44 and the amount of change of blood flow speed based on the spectrum information from the spectrum memory 20. The absolute value of blood pressure is fed to the blood pressure display 46 where it is displayed. Thus, this apparatus is able to continuously measure the absolute blood pressure in a local small vessel and deep seated artery.

I claim:

1. An ultrasonic apparatus comprising:
   a transmitter for transmitting an ultrasonic wave into a blood vessel being inspected;
   a receiver for receiving echo signals from the inside of said blood vessel;
   pulse wave propagation time measuring means for measuring the propagation time of a pulse wave between a plurality of measurement points of said blood vessel on the basis of said echo signals from said plurality of measurement points;
   pulse wave speed measuring means for calculating the speed of said pulse wave from said propagation time of said pulse wave and a distance between said measurement points;
   flow speed measuring means for measuring the flow speed of a blood flow;
   a blood pressure estimator for measuring a blood pressure at a particular time; and
   an absolute blood pressure estimator for estimating the absolute value of said blood pressure at another time different from said particular time on the basis of said blood flow speed produced from said flow speed measuring means and said blood pressure at said particular time produced from said blood pressure estimator.

2. An ultrasonic apparatus according to claim 1, wherein said blood pressure at said particular time is an end diastolic blood pressure.

3. An ultrasonic apparatus having a transmitter for transmitting an ultrasonic wave into the inside of a blood vessel being inspected, a receiver for receiving echo signals from the inside of said blood vessel, and pulse wave propagation time measuring means for calculating a propagation time of a pulse wave between a plurality of measurement points in the inside of said blood vessel on the basis of a change of Doppler signals, with respect to time, of said echo signals from said plurality of measurement points, whereby the speed of said pulse wave is calculated from said propagation time of said pulse wave and a distance between said measurement points, said ultrasonic apparatus further comprising:

a correlator for calculating a correlation function between said Doppler signals;

flow speed measuring means for estimating said propagation time of said pulse wave by use of said correlation function and determining a blood flow speed;

a blood pressure estimator for measuring a blood pressure at a particular time; and an absolute blood pressure estimator for calculating the absolute value of a blood pressure at another time different from said particular time on the basis of said blood flow speed from said flow speed measuring means and said blood pressure at said particular time from said blood pressure estimator.

4. An ultrasonic apparatus according to claim 3, wherein said blood pressure at said particular time is an end diastolic blood pressure.

5. An ultrasonic apparatus comprising:

a transmitter for transmitting an ultrasonic wave into the inside of a pipe filled with a fluid from the outside of said pipe;

a receiver for receiving echo signals from the inside of said pipe;

pulse wave propagation time measuring means for determining a propagation time of a pulse wave between a plurality of measurement points in the inside of said pipe on the basis of said echo signals from said measurement points;

pulse wave speed measuring means for calculating the speed of said pulse wave from said propagation time of said pulse wave and a distance between said measurement points;

flow speed measuring means for measuring the flow speed of said fluid within said pipe;

a pressure estimator for measuring a pressure of said fluid at a particular time; and an absolute pressure estimator for determining the absolute pressure of a fluid pressure within said pipe at another time different from said particular time on the basis of said fluid flow speed within said pipe which is obtained from said flow speed measuring means and said pressure at said particular time from said pressure estimator.

6. An ultrasonic apparatus according to claim 5, wherein said fluid is a liquid which is pressed to be fed into the inside of said pipe by a pump.

7. An ultrasonic apparatus having a transmitter for transmitting an ultrasonic wave into the inside of a pipe filled with a fluid from the outside of said pipe, a receiver for receiving echo signals from the inside of said pipe, and a pulse wave propagation time measuring means for estimating a propagation time of a pulse wave between a plurality of measurement points in the inside of said pipe from variations of Doppler signals, with respect to time, of said echo signals at said measurement points, whereby the speed of said pulse wave is calculated from said propagation time of said pulse wave and a distance between said measurement points, said ultrasonic apparatus further comprising:

a correlator for calculating a correlation function between said Doppler signals;

flow speed measuring means for estimating said pulse wave propagation time by use of said correlation function and calculating the speed of said fluid in the inside of said pipe;

a pressure estimator for measuring a fluid pressure in the inside of said pipe at a particular time; and an absolute pressure estimator for calculating the absolute value of a fluid pressure in the inside of said pipe at another time different from said particular time on the basis of the flow speed of said fluid in the inside of said pipe which is produced from said flow speed measuring means and said pressure at said particular time from said pressure estimator.

8. An ultrasonic apparatus according to claim 7, wherein said fluid is a liquid which is pressed to be fed into the inside of said pipe by a pump.

* * * * *